United States Patent [19]

Cera

[11] Patent Number: 5,301,431
[45] Date of Patent: Apr. 12, 1994

[54] HAND-HELD CUTTING TOOL
[75] Inventor: Jonel Cera, Corona, Calif.
[73] Assignee: ETM Corporation, Monrovia, Calif.
[21] Appl. No.: 983,880
[22] Filed: Dec. 1, 1992
[51] Int. Cl.[5] .................. B26B 13/00; B26B 17/00
[52] U.S. Cl. ........................................ 30/254; 30/186
[58] Field of Search .................. 30/186, 191, 193, 254, 30/346.53, 346.54, 346.55, 346.61

[56] References Cited
U.S. PATENT DOCUMENTS

| | | | |
|---|---|---|---|
| 1,955,134 | 4/1934 | Kowalski | 30/186 |
| 2,529,949 | 11/1950 | Jones et al. | 30/186 |
| 2,745,177 | 5/1956 | Kortick | 30/186 |
| 3,480,483 | 11/1969 | Wilkinson | 30/346.53 |
| 3,774,703 | 11/1973 | Sanderson | 30/346.53 |
| 3,802,078 | 4/1974 | Denes | 36/346.53 |
| 3,915,757 | 10/1975 | Engel | 30/346.55 |
| 4,453,987 | 6/1984 | Arai et al. | 30/346.53 |

Primary Examiner—Richard K. Seidel
Assistant Examiner—Paul M. Heyrana, Sr.
Attorney, Agent, or Firm—Christie, Parker & Hale

[57] ABSTRACT

A hand-held cutting tool can make repeated precision cuts into hard materials after being repeatedly exposed to highly corrosive and oxidizing conditions. The cutting tool comprises a pair of interactive stainless steel complementary members, each member having a handle portion at one end and a cutting portion at the other end. The cutting portion comprises a hardened tool-steel insert forming the tool's cutting edge. The surface of each member is hard chrome plated except for the hardened tool-steel cutting edge. Each member comprises a recessed portion of complementary size and configuration to accommodate interaction between the members. A washer resides between each member to accommodate unwanted space and a screw is used to hingedly join each member together so that the cutting edges are aligned in an opposed fashion directed toward each other. The tool's cutting portion, including both cutting edges are coated with a refractory material.

17 Claims, 3 Drawing Sheets

HAND-HELD CUTTING TOOL

FIELD OF THE INVENTION

This invention relates to hand-held cutting tools for making repeated precision cuts of hard materials after being repeatedly subjected to extremely corrosive conditions without adversely affecting the tool appearance and cutting ability.

BACKGROUND OF THE INVENTION

Hand-held cutting tools or instruments used to cut a variety of objects are known in the art. For example, a pair of scissors or shears is a hand-held cutting tool used to cut relatively softer types of materials such as paper, plastics or cloth and the like. This type of hand-held cutting tool is particularly useful for cutting materials that offer very little resistance to being cut, and thus require very little force to initiate a cut. These cutting tools, however, are of limited application and are not well suited for cutting hard objects such as metals or ceramics and the like that require a greater degree of force to initiate the cutting operation.

Hand-held cutting tools that are used to cut harder materials are configured differently from those used to cut the relatively softer materials, and are usually made from a harder material in order to endure repeated cuts. For example, a hand-held cutting tool used to cut through metal wire is configured similar to a pair of pliers having the characteristic handle and jaw arrangement. However, unlike pliers, this type of cutting tool comprises a pair of opposed cutting edges instead of opposed gripping members. The cutting tool configuration is dictated by the large force that must be applied to the cutting edges to cut a hard metal object. The tool's long handles and hinged jaw arrangement positioned near the opposed cutting edges facilitates the transfer of force needed to cut through a hard metal object.

Such hand-held cutters are known in the art and are used in a variety of manufacturing applications as well as medical and dental applications where hard materials must be cut with some degree of precision. In the area of electronics manufacturing, such cutting tools are used to cut metal wires used for making critical electrical connections and the like. In in the area of orthodontics, such cutting tools are used to make precision cuts through orthodontic arch wire used with orthodontic brackets for straightening teeth. A cutting tool used in such a manufacturing, dental or medical application must possess characteristics that exceed those of cutting tools used to perform cuts on hard materials in other less exacting applications.

A cutting tool that is used in a medical or dental procedure must operate smoothly to enable the user to make a precise cut during each use. The cutting edge of the tool must be capable of retaining its sharpness, permitting the user to use the tool repeatably without loss of cutting ability. The cutting tool must also be capable of withstanding repeated sterilizations without adversely affecting the tool's performance ability and preferably without affecting its appearance.

Hand-held cutting tools that are used in medical, dental, or high quality manufacturing applications for cutting hard materials are known in the art. Such cutting tools are configured in the plier-like arrangement for the purpose of transferring to the cutting edge of the tool the amount of force required to cut hard materials. The cutting tool is manufactured from stainless steel to enhance resistance to corrosion during repeated use and sterilization. However, stainless steel is a relatively soft metal that does not hold up well to the repeated cutting of hard metals. Therefore, cutting tools made from stainless steel are known to contain hardened tool-steel inserts that serve as the cutting edge. The hardened tool-steel inserts permit the tool to make repeated cuts of hard materials without requiring frequent sharpening.

In the past, such a cutting tool would permit a user to make repeated cuts of relatively hard materials after repeated sterilizations without a significant loss in the tool's performance capabilities. However, in today's society and the heightened awareness of AIDS and the HIV virus, tools and instruments used during any medical or dental procedure must now undergo more extensive sterilization than ever before. In the past, it was sufficient that tools or instruments used for relatively minor dental or medical procedures only undergo a cold sterilization that consisted of simply wiping or soaking the instrument with isopropyl alcohol and the like.

Today, however, a tool or instrument used during any medical or dental procedure must undergo an extensive sterilization process similar to that mandated under FDA regulations for a tool or instrument used during a surgical procedure. The newly mandated FDA sterilization procedures require that the tool or instrument be subjected to high temperature autoclaving, chemical claving, or dry heat treatment. Accordingly, cutting tools used during medical or dental procedures must now be capable of retaining their ability to perform precise cuts after repeated uses and sterilization under the new more extreme sterilization procedures.

The development of new technologies has also permitted the use of new metal compositions that are much harder than those metal compositions known before. Many of these new metal compositions are finding medical and dental application due to their unique physical properties. Therefore, cutting tools that are used during medical or dental procedures incorporating such new metal compositions must possess increased hardness enabling the cutting tool to preform repeated cuts without loss of cutting ability.

The hand-held cutting tools known in the art preform adequately when used to cut old-technology metals after being subjected to the old cold method of sterilization. However, these tool do not retain their cutting performance when subjected to the repeated cutting of new technology metals and the more extreme methods of sterilization. Typical new technology metals used in dental or medical applications have a Rockwell C hardness of approximately 50 to 60 which is only slightly less than that of the hardened tool-steel inserts forming the tool cutting edges. Therefore, each use of the tool adversely affects the sharpness of the cutting edges, and thus the ability to perform repeated precision cuts without frequent sharpening.

In addition, stainless steel cutting tools known in the art also display high instances of corrosion after being subjected to repeated sterilizations under the newly mandated procedures. This corrosion makes the tool unfit for use in manufacturing, medical and dental applications because it ultimately impairs the tool operation and its ability to perform a precision cut. Additionally, the continued use of a corroded cutting tool in a dental or medical application may pose the threat of contamination or infection through contact with an open incision.

Corrosion occurs throughout the surface of the cutting tool. However, the corrosion most notably affects the interactive movement of the tool's cutting members and the cutting edge of the tool itself. Corrosion causes the once smooth and precise interactive movement of the tool's cutting members to bind during the cutting operation, making the tool difficult and awkward to operate.

Corrosion along the hardened steel cutting edges causes them to deteriorate, adversely affecting the tool's ability to cut. Although the life of the cutting tool may be extended by frequent sharpening, this is inconvenient because it prevents the user from using the tool while it is returned to the manufacturer to be sharpened. Also, a higher likelihood exists that the tool will inadvertently be used after it is dull when the tool is one requiring frequent sharpening. The potential harm that could result from using a dull cutting tool to initiate a cut where precision is called for outweighs the utility of a cutting tool requiring frequent sharpening. Finally, the extent of such sharpening is ultimately limited by the thickness of the hardened metal coating.

In an attempt to increase the cutting tool's corrosion resistance and enhance the hardness of its cutting edge, cutting tools have been known to be plated with hard chrome. Hard chrome is selected as the plating material because of its characteristic hardness and ability to resist corrosion. In practice, cutting tools plated with hard chrome display better corrosion resistance throughout the body of the tool than plain stainless steel cutting tools. However, cutting tools plated with hard chrome are unable to retain their coating at the cutting edge where such corrosion resistance and enhanced hardness is critical. Shortly after use, the hard chrome plating at the cutting edge of the tool flakes off and away from the cutting edge leaving exposed the bare hardened tool-steel insert. The hard chrome flaking is believed to be caused by the lack of surface area at the tip of the cutting edge necessary for adherence. After the hard chrome plating has flaked away, the cutting edge undergoes corrosion that causes the cutting edge to deteriorate, adversely affecting the sharpness of the cutting edge and the tool's ability to cut.

Once the hard chrome plating has flaked away from the cutting edge, repeated use and sterilization of the tool causes corrosion to form underneath the remaining hard chrome plating, causing the stainless steel body of the tool to deteriorate. As the corrosion progresses, there exists the additional danger of contamination or bodily infection that may result from the hard chrome plating flaking off and falling into an open incision during a medical or dental procedure.

It is, therefore, desirable to provide a hand-held cutting tool for use in medical, dental, or high quality manufacturing applications having a cutting edge with enhanced hardness to permit its repeated use with metals, ceramics or other material compositions having a high hardness. It is also desirable that the cutting tool have enhanced corrosion resistance throughout its surface and at its cutting edge enabling the tool to withstand repeated sterilizations under the more extreme FDA mandated conditions.

The hand-held cutting tool should be capable of precise operation enabling a user to make precision cuts with the tool. Finally, the cutting tool should be manufactured by known commercial methods permitting cost effective production and sales of the product.

SUMMARY OF THE INVENTION

Toward this end, the present invention provides a hand-held cutting tool comprising a pair of complementary interactive members made from stainless steel or a suitable tool steel. Each complementary member has a handle portion at one end and a cutting portion at its other end. The cutting portion further comprises a hardened tool-steel insert that forms the cutting edge. A preferred hardened tool steel is T-15. Each member has a recessed portion near its cutting portion that is configured to complement, accommodate and permit interconnection with the recessed portion the other member. A washer is inserted between the recessed portions of the complementary members to accommodate any unwanted spatial tolerance between the members. A screw made from stainless steel is used to hingedly join together both members at their recessed portion. The complementary members are joined together with their cutting edges aligned in an opposed fashion and directed toward each other.

Before being joined, both complementary members are prepared and hard chrome plated by known commercial methods. The entire surface area of each member is hard chrome plating except for the cutting edge. The thickness of the hard chrome plating is in the range of from 0.02 to 0.03 millimeters. After plating, complementary members are joined together and the cutting edges are sharpened. The tool is prepared and the tool's cutting portion, including both cutting edges, is coated with a refractory hard material using known commercial methods. The refractory material is selected from the group consisting of nitrides, carbides and carbonitrides of refractory metals. Exemplary refractory metals include titanium, tantalum, tungsten, chromium, hafnium and silicon. The preferred refractory material is titanium nitride and the preferred coating thickness is in the range of from two to five micrometers.

BRIEF DESCRIPTION OF THE DRAWINGS

These and other features and advantages will become appreciated as the same becomes better understood with reference to the specification, claims and drawings wherein:

DETAILED DESCRIPTION OF THE INVENTION

Figure 1:
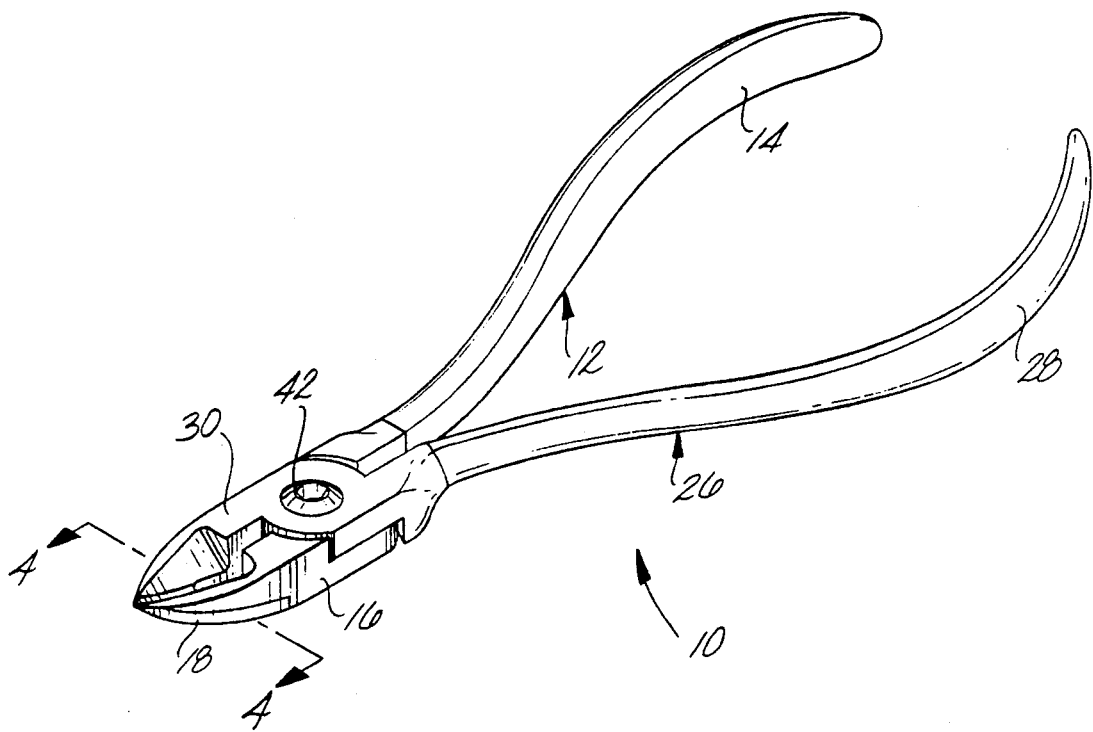
FIG. 1 is a perspective view of a preferred embodiment of the present invention illustrating the invention in its assembled state.
Figure 2:
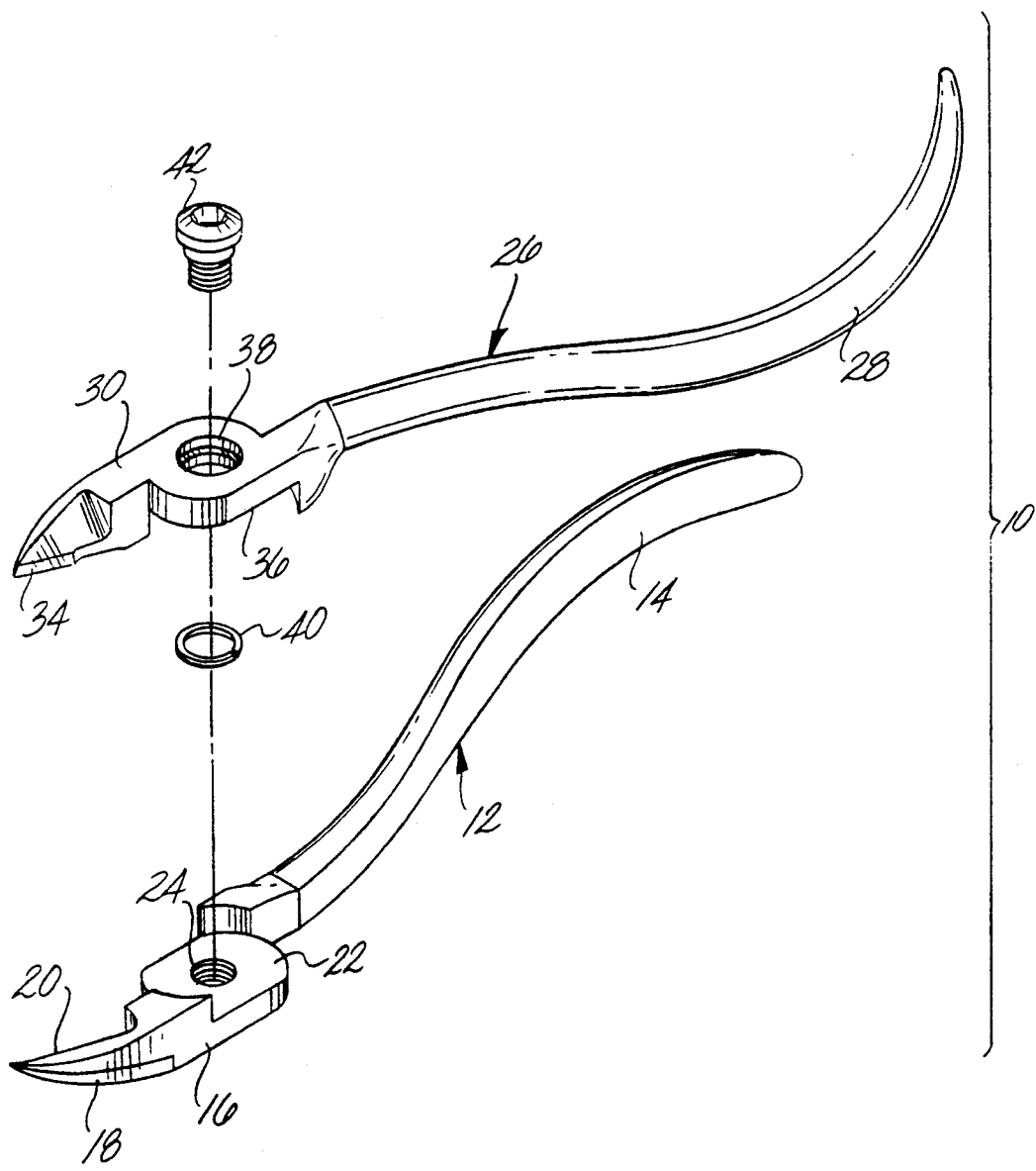
FIG. 2 is a perspective view of a preferred embodiment of the present invention illustrating the invention in its disassembled state.

FIGS. 1 and 2 show the preferred embodiment of a hand-held cutting tool 10 according to the present invention. The tool comprises a pair of complementary hingedly interactive members 12 and 26. First member 12 may be made from carbon steel, stainless steel, tool steel or any other type of metal or metal alloy appropriate for use as a tool. Preferably, the first member is made from type 416 stainless steel. The first member comprises a handle portion 14 at one of its ends and a cutting portion 16 at its other end. The handle portion is slightly curved near its end to enable a user to grip the tool by hand without causing discomfort. Cutting portion 16 comprises a hardened tool-steel insert 18 that is nickel brazed to the first member to form a cutting edge 20. The insert may be made from any hardened tool steel suitable for cutting hard materials. Preferably, the insert is made from type T-15 tool steel having a Rockwell C hardness of approximately 62.

As most clearly shown in FIG. 2, a recessed portion 22 is located proximate the first member's cutting portion 16. A threaded hole 24 is located near the center of the recessed portion and extends completely through the thickness of the first member.

A second member 26 is configured as the mirror image and complementary to the first member 12 and may be made from carbon steel, stainless steel, tool steel or any other type of metal or metal alloy appropriate for use as a tool. Preferably, the second member is made from type 416 stainless steel. The second member comprises a handle portion 28 at one of its ends and a cutting portion 30 at its other end. Like the handle portion 14 of the first member, handle portion 28 is slightly curved proximate the end to provide a comfortable grip during use. Cutting portion 30 also comprises a hardened tool-steel insert 32 that forms the second member's cutting edge 34. The insert may be made from any hardened tool steel suitable for cutting hard materials. Preferably, the insert is made from type T-15 tool steel having a Rockwell C hardness of approximately 62. The second member comprises a recessed portion 36 of sufficient size and configuration to accommodate interaction with the recessed portion 22 of the first member, see FIG. 2. An unthreaded hole 38 is located near the center of the recessed portion and extends completely through the thickness of the second member. The hole has a diameter approximately similar to that of threaded hole 24.

As shown in FIG. 2, a washer 40 is of sufficient size and thickness to permit its placement between the recessed portions of the first and second members. The washer may be made from carbon steel, stainless steel, or any other type of metal or metal alloy appropriate for use as a tool. Preferably, the washer is made of type 304 stainless steel and is of sufficient thickness to accommodate any unwanted spatial tolerance that might exist after the complementary members are joined together.

A screw 42 is of sufficient size and diameter to permit threadable engagement with the threaded hole 24 of the first member. The screw may be made from carbon steel, stainless steel, or any other type of metal or metal alloy appropriate for use as a tool. Preferably, the screw is made from type 304 stainless steel.

The first and second members are joined together by inserting the washer into the recessed portion of the first member such that the washer's hole is aligned with the threaded hole 24, see FIG. 2. The recessed portion of the second member is placed over and within the recessed portion of the first member so that the hole 38 is aligned with the threaded hole 24. The screw 42 is then inserted into the hole, through the washer and is threadably engaged within the threaded hole. The screw permits the complementary hingable interaction of the first and second members.

Figure 3:
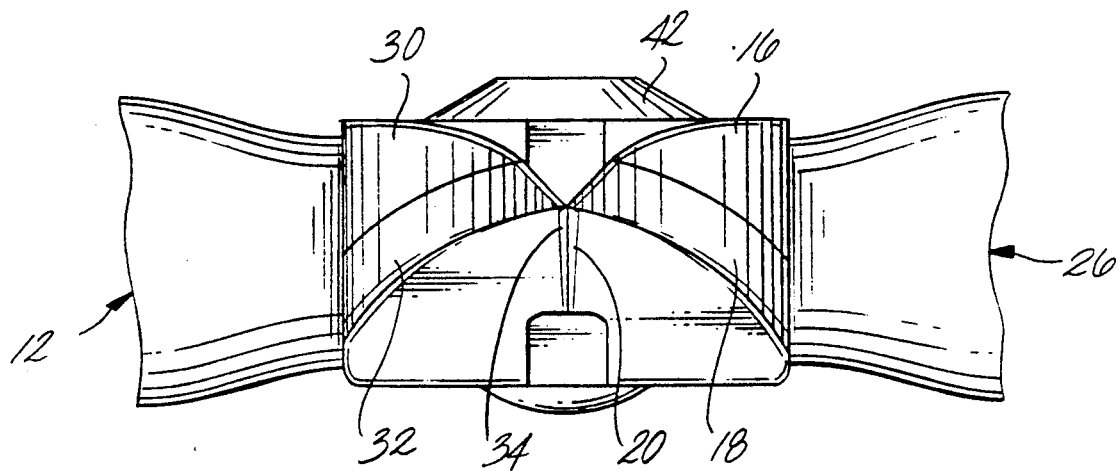
FIG. 3 is a frontal view of a preferred embodiment of the present invention illustrating the cutting portion of the invention and the use of hardened tool-steel inserts for the cutting edges.

As best shown in FIG. 3, the cutting edges of the joined members are aligned in an opposed fashion and directed toward each other. The alignment of the cutting edges is important to the cutting performance of the tool. In order to ensure optimum cutting performance, the two cutting edges should be aligned within two to 4 micrometers. Washer 40 serves to accommodate any unwanted spatial tolerance between the two members and ensure that the preferred alignment exists.

The tool is used to cut a hard material object such as a metal wire and the like by the user gripping the handle ends of the tool and positioning the object to be cut between the tool's cutting edges. The user then squeezes both handle ends together causing the hand force to be transferred from the handles, through the hinged attachment to the cutting edges of the tool causing the object to be cut.

Figure 4:
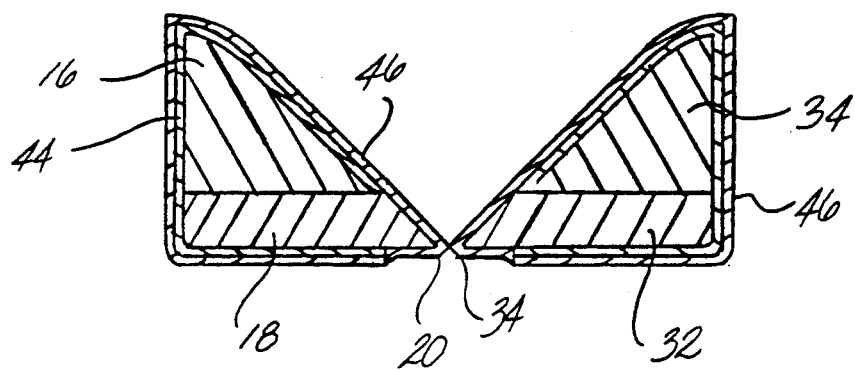
FIG. 4 is cross section on line 4—4 of FIG. illustrating the cutting portion of the invention and the different materials comprising the cutting portion and the cutting edges.

Before being hingedly joined together, the first and second members are first prepared and then plated with hard chrome plating 44, as best shown in FIG. 4. The members are prepared for hard chrome plating by known commercial methods of heat treating and then polishing to about a 0.4 micrometer finish. After polishing, the members undergo a commercially available degreasing process such as ultra sound or solvent cleaning and the like. The surface of the members are then plated with hard chrome by commercially known methods such as electroplating and the like. The entire surface of each complementary member is hard chrome plated except a small area at the cutting edge of each member, which is masked by known commercial methods, see FIG. 4. The cutting edges are not hard chrome plated because hard chrome plating is known to flake off and away from the cutting edge during use. Further, electing not to plate the cutting edge prevents potential corrosion from occurring underneath the hard chrome plating, resulting from the lifting or flaking of the plating at the cutting edge. The preferred thickness of hard chrome plating is in the range of from 0.02 to 0.03 millimeters.

Hard chrome is selected as a desirable plating material because of its known resistance to wear, abrasion and corrosion. The hard chrome plating enhances the corrosion resistance of the tool, enabling it to withstand repeated sterilizations under newly mandated FDA regulations. FDA regulations require that all instruments used in a dental or medical procedure undergo either chemical claving, autoclaving or dry heat sterilization after each use Autoclaving comprises subjecting the instrument to steam heat of approximately 275° F. for a set period of time. Chemical claving comprises subjecting the instrument to highly oxidizing chemicals for a set period of time. Dry heat comprises heating the instrument to approximately 365° F. for about 6 minutes. Cutting devices plated with hard chrome have displayed improved corrosion and oxidation resistance under these conditions. Bare stainless steel shows staining and can appear discolored after autoclaving.

The hard chrome plating also facilitates the smooth hingable interaction of the complementary members by enhancing the wear resistance of the recessed portions of each member. Additionally, the hard chrome plating enhances the hardness of the cutting device, yielding a device having a Rockwell C hardness of approximately 78-80 at its surface.

After the hard chrome plating, both complementary members are hingedly joined together by screw 42 and both cutting edges are sharpened. The tool is then prepared for coating with a refractory material 46 by commercially available methods such as heat treating, etching, ultra sound, solvent cleaning and the like. The tool is coated with a refractory material to improve the corrosion resistance and hardness of the cutting edge, as best shown in FIG. 4. A refractory material is chosen as the coating composition because of its inherent corrosion resistance and hardness. The refractory metal is selected from the group consisting of nitrides, carbides, and carbonitrides of refractory metals. The preferred refractory material is titanium nitride (TiN). The device is coated with TiN using commercially available processes such as physical vapor disposition, chemical vapor disposition, ion sputtering and the like. TiN is a golden colored refractory material, thus, the portion of the device coated with TiN is readily identifiable by its golden color.

The preferred thickness of the TiN coating is in the range of from two to five micrometers. A TiN thickness of less than about two micrometers or greater than about five micrometers results in an irregular or uneven coating that fails to optimally enhance the corrosion resistance and hardness of the hardened steel cutting edges. As best shown in FIG. 4, it is preferred that only the cutting portion, including the cutting edges of the tool be coated with TiN because the cutting edges require enhanced hardness and corrosion resistance that cannot otherwise be provided by hard chrome plating.

Unlike hard chrome plating, the TiN coating does not flake away from the cutting edge surface. The TiN coating increases the hardness of the hardened tool-steel cutting edges from a Rockwell C hardness of approximately 62 to approximately 84. The increased hardness allows the user to make repeated cuts with the device on hard objects such as orthodontic arch wire made from hard nickel alloy or ceramic materials and the like without adversely affecting the cutting performance of the tool.

Surprisingly, it has been shown that the ease of cutting is enhanced by having the TiN layer in the cutting edges as compared with bare metallic cutting edges. It is believed that coating the cutting edge with TiN facilitates the cutting of hard metals by reducing the friction associated with a metal object to metal cutting edge interface. Finally, TiN coating the hard chrome plated portion of the tool increases the Rockwell C hardness from approximately 78–80 to approximately 84.

It is to be understood that although only one exemplary embodiment of the hand-held cutting tool has been described and illustrated herein, many variations will be apparent to those skilled in the art. For example, the entire device may be coated with TiN instead of just coating the device's cutting portion and cutting edges. In such an embodiment the entire surface of the device would be a golden color.

Alternative embodiments of the invention may be used for applications other than medical or dental procedures where a hand-held cutting tool having an enhanced cutting ability and corrosion resistance is required. For example, the cutting device may be used in the electronics industry where hard materials such as wire and the like are repeatedly cut under exacting conditions. In such industries a premium is placed upon the ability to repeatedly perform a precision cut, therefore, a premium is placed upon a cutting tool that retains its ability to perform. Further, cutting operations in the electronics industry are often performed in so called clean rooms where a hand-held cutting tool must display a high degree of corrosion resistance to minimize associated contamination.

An alternative embodiment of the invention may be configured differently than that of the exemplary embodiment, however, still have interactive cutting edges made from hardened steel and coated with TiN to increase the corrosion resistance and hardness of the cutting edge. Still another embodiment of the invention may simply comprise a single edged hard chrome plated cutting tool having its cutting edge made from hardened tool steel and coated with a suitable refractory material of the nitride, carbide or carbonitride group.

Since many such modifications may be made, it is to be understood that within the scope of the following claims, this invention may be practiced otherwise than specifically described.

What is claimed is:

1. A hand-held cutting tool comprising:
   a member having a handle portion at one end and a cutting portion at its other end;
   a hardened tool-steel insert attached to the cutting portion comprising a cutting edge;
   the surface of the member having a hard chrome plating except for the cutting edge; and
   the cutting edge having a refractory material coating.

2. A hand-held cutting tool as recited in claim 1, wherein the thickness of the hard chrome plating is in the range of from 0.02 to 0.03 millimeters.

3. A hand-held cutting tool as recited in claim 1, wherein the refractory material used to coat the member is selected from the group consisting of nitrides, carbides and carbonitrides of refractory metals.

4. A hand-held cutting tool as recited in claim 3, wherein the refractory material is titanium nitride and the thickness of the coating is in the range of from two to five micrometers.

5. A hand-held cutting tool for performing repeated cutting operations on hard materials, the cutting tool comprising:
   a pair of interactive complementary members, each complementary member having at one of its ends a handle portion and having at its other end a cutting portion, each cutting portion further comprising a hardened steel cutting edge, the complementary members having a hard chrome plated surface except along each hardened steel cutting edge, the complementary members having a refractory material coating limited to the cutting portion that includes each cutting edge; means for joining the complementary members together so that the cutting edge of each member is aligned in an opposed fashion and directed toward the other cutting edge.

6. A hand-held cutting tool as recited in claim 5, wherein the interactively opposed complementary members are made from stainless steel.

7. A hand-held cutting tool as recited in claim 5, wherein the hardened steel cutting edge comprises a type T-15 tool-steel insert brazed into each complementary member.

8. A hand-held cutting tool as recited in claim 5, wherein the thickness of the hard chrome plating is in the range of from 0.02 to 0.03 millimeters.

9. A hand-held cutting tool as recited in claim 5, wherein the refractory metal used to coat the complementary member is selected from the group consisting of nitrides,, carbides and carbonitrides of refractory metals.

10. A hand-held cutting tool as recited in claim 9, wherein the refractory metal is titanium nitride and the thickness of the coating is in the range of from about two to five micrometers.

11. A hand-held cutting tool that is able to withstand repeated cutting of hard materials after being repeatably subjected to extremely corrosive and oxidizing conditions without significant decrease in cutting performance or surface deterioration, the cutting tool comprising:
a pair of interactive complementary members, each complementary member being made of stainless steel and having a handle portion at one of its ends and a cutting portion at its other end, the cutting portion further comprising a hardened tool-steel insert for a cutting edge, each member being hard chrome plated except for the hardened tool-steel cutting edge, the hard chrome plating having a thickness in the range of from 0.02 to 0.03 millimeters, a portion of each member including the hardened tool-steel cutting edge being coated with titanium nitride having a thickness of from two to five micrometers.

12. A hand-held cutting tool for repeatedly cutting hard materials where the tool is repeatedly exposed to highly corrosive conditions, the tool comprising:
a first member having a handle at one of its ends and a cutting edge at its other end, the first member having a recessed portion near the cutting edge, the recessed portion of the first member having a threaded hole near its center, the first member being made out of stainless steel and having a hardened tool-steel insert comprising its cutting edge, the first member being plated with hard chrome except for the cutting edge, the cutting edge of the first member being coated with a refractory material;
a second member having a handle at one of its ends and a cutting edge at its other end, the second member configured as the mirror image of and complementary to the first member, the second member having recessed portion near the cutting end and configured to accommodate interaction with the recessed portion of the first member, the recessed portion of the second member having an unthreaded hole near its center sized approximately similar to the threaded hole in the first member, the second member being made out of stainless steel and having a hardened tool-steel insert comprising its cutting edge, the second member being plated with hard chrome except for its cutting edge, the cutting edge of the second member being coated with a refractory material;
means for accommodating any unwanted spatial tolerance between the first and second members; and
means for joining the first and second members together.

13. A hand-held cutting tool as recited in claim 12, wherein the first and second members are made from type 410 stainless steel.

14. A hand-held cutting tool as recited in claim 12, wherein the hardened steel cutting edge of each member comprises type T-15 tool steel having a Rockwell C hardness of approximately 62.

15. A hand-held cutting tool as recited in claim 12, wherein the hard chrome plating is in the range of from 0.02 to 0.03 millimeters.

16. A hand-held cutting tool as recited in claim 12, wherein the refractory material is selected from the group consisting of nitrides, carbides and carbonitrides of refractory metals.

17. A hand-held cutting tool as recited in claim 16, wherein the refractory metal selected is titanium nitride and the thickness of the coating is in the range of from about two to five micrometers.

* * * * *